(12) United States Patent
Philippe et al.

(10) Patent No.: US 8,765,107 B2
(45) Date of Patent: Jul. 1, 2014

(54) PROCESS FOR STRAIGHTENING KERATIN FIBRES WITH A HEATING MEANS AND DENATURING AGENTS

(75) Inventors: Michel Philippe, Wissous (FR); Gérard Malle, Villiers S/Morin (FR); Philippe Barbarat, Bois-Colombes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/369,516

(22) Filed: Feb. 9, 2012

(65) Prior Publication Data

US 2012/0192888 A1    Aug. 2, 2012

Related U.S. Application Data

(63) Continuation of application No. 12/302,252, filed as application No. PCT/FR2007/000870 on May 23, 2007, now abandoned.

(60) Provisional application No. 60/814,529, filed on Jun. 19, 2006.

(30) Foreign Application Priority Data

May 24, 2006   (FR) ...................................... 06 51911

(51) Int. Cl.
  *A61K 8/00*   (2006.01)
  *A61K 8/42*   (2006.01)
  *A61K 8/365*  (2006.01)
  *A61Q 5/04*   (2006.01)

(52) U.S. Cl.
  CPC . *A61K 8/42* (2013.01); *A61K 8/365* (2013.01); *A61Q 5/04* (2013.01)

USPC ........................................................ 424/70.2

(58) Field of Classification Search
  None
  See application file for complete search history.

(56) References Cited

U.S. PATENT DOCUMENTS

| 5,635,168 A * | 6/1997 | Burns et al. .................. 424/70.4 |
| 2006/0127337 A1 * | 6/2006 | Radisson ..................... 424/70.2 |

FOREIGN PATENT DOCUMENTS

| EP | 1 752 130 A1 | 2/2007 |
| JP | 2003-212737 | 7/2003 |
| JP | 2006-016391 | 1/2006 |

OTHER PUBLICATIONS

English translation of Japanese Office Action for Japanese Application No. 2009-511549, dated Mar. 15, 2012(4 pages).
Patent Abstracts of Japan for JP Publication No. 2003-212737 in English (1 page).

* cited by examiner

*Primary Examiner* — Brian Gulledge
(74) *Attorney, Agent, or Firm* — The Marbury Law Group, PLLC

(57) ABSTRACT

The invention relates to a process for straightening keratin fibers, comprising: (i) a step in which a straightening composition containing at least two denaturing agents is applied to the keratin fibers, (ii) a step in which the temperature of the keratin fibers is raised, using a heating means, to a temperature of between 110 and 250° C.

8 Claims, No Drawings

PROCESS FOR STRAIGHTENING KERATIN FIBRES WITH A HEATING MEANS AND DENATURING AGENTS

CROSS-REFERENCE TO RELATED APPLICATIONS

This is a continuation of application Ser. No. 12/302,252, filed May 18, 2009, and claims the benefit of French Patent Application No. 0651911, filed May 24, 2006, and the benefit of U.S. Provisional Application No. 60/814,529, filed Jun. 19, 2006, all of which are incorporated herein by reference.

The invention relates to a process for relaxing keratin fibres with a heating means and at least two denaturing agents.

The relaxing process according to the invention is performed without using a reducing agent or a lanthionization agent. It does not comprise any reducing or lanthionizing step.

According to the invention, the term "keratin fibres" means fibres of human or animal origin such as head hair, bodily hair, the eyelashes, wool, angora, cashmere or fur. Although the invention is not limited to particular keratin fibres, reference will nevertheless be made more particularly to head hair.

According to the invention, the term "relaxing" covers the relaxing, straightening or uncurling of Caucasian or African hair.

The term "denaturing agent" means a compound of organic or mineral origin containing both at least one electron-donating site of basic or nucleophilic nature and at least one electron-accepting site of acidic or electrophilic nature, which interacts with the weak bonds of keratin.

According to the invention, a denaturing agent is a compound capable of reducing the optical rotation of a model protein, for instance bovine serum albumin, by at least 7° and/or 5° at 579 nm, the measurements being taken after incubation for 3 hours at 37° C., using a polarimeter, as described in Biochemistry 2 (1), 47-57, 1963:
  either in TRIS 0.05 M pH 7.6 buffer
  or in a 5.45 M urea solution when the solubility of the compound is insufficient in the TRIS 0.05 M pH 7.6 buffer.

The compound is considered as being a denaturing agent according to the invention if the reduction of the optical rotation is at least 7° in TRIS 0.05 M pH 7.6 buffer and/or at least 5° in 5.45 M urea solution.

The term "weak bonds of keratin" means all the non-covalent bonds such as:
  the saline bonds resulting from coulombic interactions between the functional groups present on the side chains of amino acids
  the hydrogen bonds that become established between amino acids especially via oxygen and hydrogen atoms
  the hydrophobic bonds resulting from the tendency of the non-polar chains of amino acids to associate in order to minimize the contacts with water.

The term "heating means" means any means for heating keratin fibres to a temperature of at least 110° C., such as heating irons, for example flat or round irons, microwave generators or sources of infrared radiation.

Two techniques are used for permanently reshaping the hair. They are based on cleavage of the disulfide covalent bonds present in keratin (cystine):
  the first consists, in a first stage, in performing this opening of the disulfide bonds using a composition containing a reducing agent, and then, after having preferably rinsed the hair, in reconstituting the said disulfide bonds in a second stage, by applying to the hair, which has been placed under tension beforehand with rollers or the like or shaped or straightened out by other means, an oxidizing composition also known as a fixer, so as to give the head of hair the desired shape. This technique makes it possible either to make the hair wavy or to relax it, uncurl it or straighten it out;
  the second consists in performing a "lanthionization" operation using a composition containing a base belonging to the hydroxide family. This leads to replacement of the disulfide bonds (—CH2-S—S—CH2-) with lanthionine bonds (—CH2-S—CH2-). This lanthionization operation involves two consecutive chemical reactions:
  the first reaction consists of a beta-elimination on cystine brought about by a hydroxide ion, leading to the cleavage of this bond and to the formation of dehydroalanine:

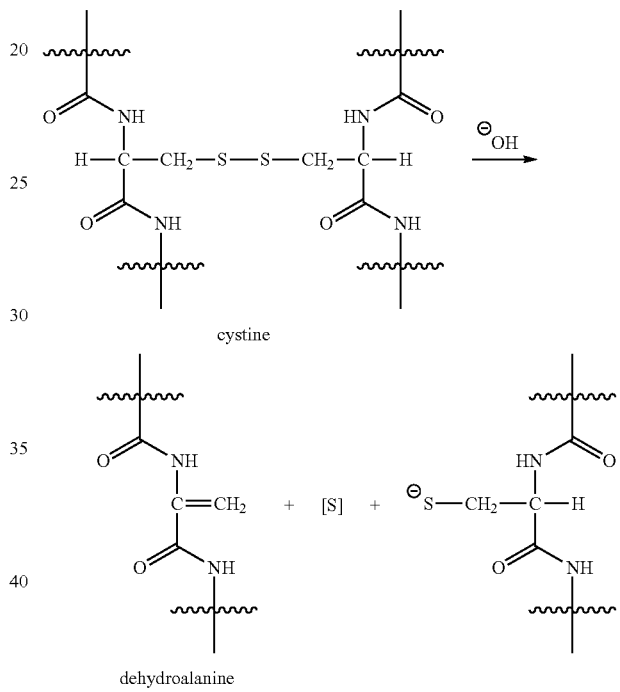

the second reaction is a reaction of dehydroalanine with a thiol group. Specifically, the double bond of the dehydroalanine formed is a reactive double bond. It can react with the thiol group of the cysteine residue that has been released to form a new bond referred as a lanthionine bridge or bond or residue.

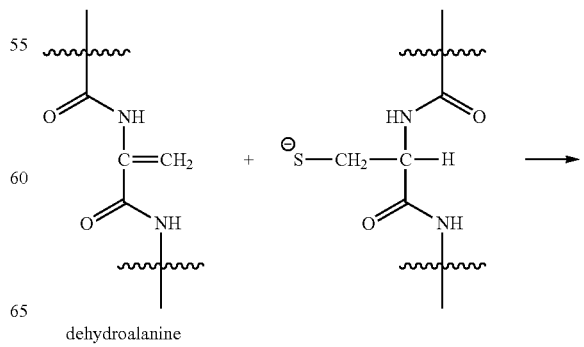

-continued

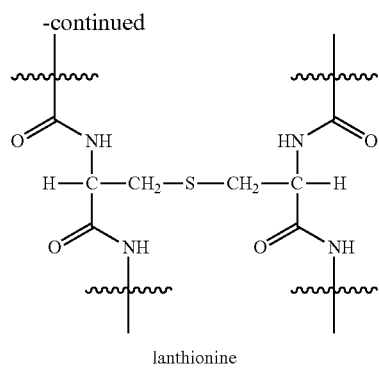

lanthionine

Relative to the first technique using a reducing agent, this lanthionization technique does not require a fixing step, since the formation of the lanthionine bridges is irreversible. It is thus performed in a single step and makes it possible either to make the hair wavy, or to relax it, uncurl or straighten it out. However, it is mainly used for relaxing naturally curly hair.

For the first technique, the reducing compositions generally used for the first step of a permanent-waving or hair-relaxing operation contain thiols, sulfites or bisulfites as reducing agent. These agents are generally used in essentially aqueous medium at concentrations of between 0.5 and 1 M to obtain good opening of the disulfide bonds. Among the thiols, those commonly used are thioglycolic acid, cysteamine, glyceryl monothioglycolate, thiolactic acid and cysteine. Thioglycolic acid is particularly efficient at reducing the disulfide bonds of keratin at alkaline pH, especially in the form of ammonium thioglycolate, and constitutes the product most frequently used in permanent waving ("hair waving"). It has been found, however, that thioglycolic acid must be used in sufficiently basic medium (in practice at a pH of between 8.5 and 9.5) if curling of satisfactory intensity is to be obtained. Besides the drawback of releasing an unpleasant odour requiring the use of more or less efficient fragrances to mask the odours, the use of a thiol at alkaline pH also results in degradation of the fibre and most particularly in impairment of artificial colorations.

Sulfites or bisulfites are mainly used for relaxing the hair. They have drawbacks similar to those of thiols, with lower efficacy.

Thiols and sulfites (or bisulfites) also have the drawback of having poor stability in aqueous solution.

In general, the durability of the reshaping effects obtained with thiols and sulfites by reduction of disulfides following by fixing is judged to be very much lower than that which may be obtained via the lanthionization technique.

For the second technique, the compositions generally used to perform lanthionization contain as base a hydroxide such as sodium hydroxide, guanidinium hydroxide or lithium hydroxide. These lanthionization active agents, which allow opening of the disulfide bonds via a beta-elimination mechanism, are generally used as a water-oil emulsion at concentrations of between 0.4 and 0.6 M, by leaving them to act generally for 10 to 15 minutes at room temperature. Sodium hydroxide remains the agent most frequently used. Guanidinium hydroxide is now the preferred compound for many compositions. These two hydroxides, sodium hydroxide and guanidinium hydroxide, are the two main agents used for the relaxing or uncurling of naturally curly hair. They have several advantages over ammonium thioglycolate and sulfites, in particular the absence of unpleasant odour, the fact that only one operating step is required (shorter treatment time) and much greater durability and efficacy of reshaping of the hair.

However, these hydroxides have the major drawback of being caustic. This causticity affects the scalp by causing irritation, which is occasionally severe. This may be partially remedied by applying beforehand to the scalp fatty protective cream often referred to as a "base" or "base cream", the word "base" in this case not having the meaning of a basic agent in the chemical sense. When the protective cream is combined with the hydroxide in a single composition, it is generally referred to as "no-base", as opposed to the above name. This "no-base" technique is preferred.

The causticity of hydroxides also affects the state of the hair by firstly giving it a coarse feel and secondly making it much more brittle, this brittleness possibly going as far as crumbling or breaking or even dissolution of the hair if the treatment is prolonged. In certain cases, hydroxides also cause decoloration of the natural colour of the hair.

Formulations containing sodium hydroxide are generally referred to as "lye relaxers" and those not containing it are referred as "no-lye relaxers".

The main relaxing formulations known as "no-lye" relaxers use guanidinium hydroxide. Since guanidinium hydroxide is unstable, it is generated at the time of use by mixing guanidinium carbonate and a source of sparingly soluble hydroxide such as calcium hydroxide. The reaction between these two compounds leads to the formation of guanidinium hydroxide and calcium carbonate, which precipitates in the composition. The presence of this precipitate makes the final rinsing of the hair much more difficult and leaves mineral particles on the hair and the scalp, which give it a coarse feel and an unaesthetic appearance resembling dandruff. The recent success of guanidinium hydroxide ("no-lye") over sodium hydroxide ("lye") appears to arise from better relaxing efficacy and better skin tolerance. However, these techniques using bases of the hydroxide family remain very aggressive to the hair and the scalp and require very strict control of the duration of application to avoid excessive irritation and impairment of the hair that may go as far as breakage. This aggressiveness arising from the causticity of hydroxides is justification for not using these hair lanthionization compositions for permanent waving (hair waving), but solely for hair straightening or hair relaxing.

Furthermore, hydroxides are known to be good agents for hydrolysing amide functions (cf. for example March's Advanced Organic Chemistry, 5th edition, Wiley Interscience, New York, "Hydrolysis of Amides" page 474 et seq.), which thus lead to cleavage of peptide bonds by direct nucleophilic attack. It is thus probable that the observed impairments of the hair and of keratin materials in the broad sense are largely due to partial hydrolysis of the amide bonds of keratin.

There is thus a real need for relaxing compositions that are markedly less aggressive to the hair.

Various studies have been conducted in order to overcome both the drawbacks of reducing agents (first technique) and/or those of hydroxides (second technique).

Thus, many reducing agents have been proposed to replace thioglycolic acid, but thioglycolic acid in the form of ammonium thioglycolate remains both the reference compound and the compound most widely used in cosmetic formulations, not only for shaping but also for straightening the hair.

It has also been proposed in numerous patents to combine common reducing agents (thiols, sulfites or bisulfites) with urea or alkyl ureas to reduce the irritation and damage caused to the hair, not only for shaping but also for relaxing. Mention will be made, for example, of:

patent application CA 1315204, which describes a composition containing ammonium thioglycolate (5.5-11.5%) and urea or a monoalkyl urea (1-3%) for shaping the hair, U.S. Pat. No. 3,847,165, which describes a composition containing ammonium thioglycolate (1.2-1.4 M) and urea (2.0-2.7 M) for shaping the hair at an acidic pH, patent application NL 6410355, which describes a composition containing a sulfite (0.8-1.5 M) and urea (0.6-3.0 M) for shaping and relaxing the hair, patent application JP 2000/229 819, which describes a composition containing a sulfite or bisulfite (0.5-15%), urea (0.5-15%) and an alcohol (ethanol and/or isopropanol, 1-30%) for shaping and relaxing the hair.

It has also been proposed in numerous patents to combine hydroxides, serving as lanthionization active agent, with certain additives generally serving to protect the hair. Mention will be made, for example, of:

patent application WO 2002/003 937, which describes a composition containing C3-C5 monosaccharides, patent application WO 2001/064 171, which describes a composition containing complexing agents, U.S. Pat. No. 5,641,477, which describes a composition containing a hydrogenated starch hydrolysate, patent application WO 02/085 317, which describes a composition containing organic nucleophiles that react during the second step with the dehydroalanine formed with hydroxides, to give new bridges.

Although all these proposals lead to more or less pronounced improvements, they are not able to sufficiently reduce the damage associated with the very causticity of hydroxides.

As indicated previously, the use of reducing agents leads to poor durability of the relaxing or straightening of the hair and the use of hydroxides, on account of their causticity, limits their use in the field of hair relaxing.

The use of resorcinol at a concentration of 40% and at a pH of 7 for relaxing the hair has been reported by M. Wong et al.: M. Wong, G. Vis-surel, and J. Epps J. Soc. Cosmet. Chem. (1994), 45, 347-352. However, the tests that we have performed under these conditions on naturally curly African hair do not relax it, but lead, at the very best, to slight uncurling.

After considerable studies, it has now been discovered, entirely surprisingly and unexpectedly, that hair can be durably relaxed by combining the action of at least two denaturing agents and of a means of heating to a temperature above 110° C. Excellent results in terms of relaxing, cosmetic properties of the hair and fibre integrity are thus obtained.

Without being bound by theory, the Applicant considers that there is a combined action, on the keratin fibres, of at least two denaturing agents and of a heating means, which allows the fibres to be efficiently and durably relaxed.

The Applicant has found that it is possible to overcome the drawbacks of the prior art and to satisfy the abovementioned objectives by performing a process for relaxing keratin fibres, comprising:

a step of applying to the keratin fibres a hair-relaxing composition containing at least two denaturing agents, a step of raising the temperature of the keratin fibres, using a heating means, to a temperature of between 110 and 250° C.

Advantageously, the denaturing agents have a molar mass of greater than 18.1 g/mol and preferably between 40 and 600 g/mol.

Preferably, the hair-relaxing composition comprises an overall concentration of denaturing agents of between 1 M and 8 M and more advantageously between 2 M and 8 M of the said denaturing agents; this corresponds to a weight concentration of between about 6% and about 80% and more advantageously between about 12% and about 80%, relative to the total weight of the composition, of the said denaturing agents.

Advantageously, the temperature is raised using a heating means to a temperature of between 120° C. and 220° C. and more advantageously between 140° C. and 220° C.

According to one embodiment, the said composition is applied to wet keratin fibres.

A step intended to remove the excess composition, for example using a towel, may also be introduced between the step of applying the composition and the step of raising the temperature.

Preferably, the denaturing agents are chosen from protein-denaturing agents such as:

ureas,
guanidines,
α-hydroxy acid and α-keto acid derivatives,
mono-, di-, tri- or polyhydroxylated aromatic derivatives,
cyclic or linear amides,
surfactants or detergents, especially those containing sugar or choline or deoxycholine or polyethylene glycol units, such as the following compounds:
acetobromo-α-D-glucose
taurodeoxycholic acid sodium salt
N-octyl-β-D-glucopyranoside
MEGA-8
N-hexyl-β-D-glucopyranoside
N-heptyl-β-D-thioglucopyranoside
N-heptyl-β-D-glucopyranoside
glycodeoxycholic acid sodium salt
sodium deoxycholate
sodium cholate
CHAPSO
CHAPS
octaethylene glycol mono-N-dodecyl ether
N,N'-bis(3-D-gluconamidopropyl)cholamide
polyoxyethylene (23) lauryl ether C12E23
nonaethylene glycol monododecyl ether
cetrimide
decyl glucoside
decyl maltoside
N,N-bis(3-D-gluconamidopropyl)deoxycholamide
digitonine
dodecyl maltoside
dioctyl sodium sulfosuccinate
lauryldimethylamine oxide
octaethylene glycol isotridecyl ether
glycocholic acid, sodium salt
sodium lauryl sulfate
octanoyl-N-methylglucamide
nonanoyl-N-methylglucamide
decanoyl-N-methylglucamide
nonyl glucoside
nonaethylene glycol octylphenyl ether
octyl thioglucoside
polyethylene polypropylene glycol
monosodium taurocholic acid
nonaethylene glycol octylphenyl ether
polyoxyethylene sorbitan monolaurate
polyoxyethylene sorbitan monooleate
N-octylsulfobetaine
N-decylsulfobetaine
N-dodecylsulfobetaine
N-hexyldecylsulfobetaine,
amidines, such as acetamidine hydrochloride, thioureas, urethanes, alcohols, polyols, amine oxides such as N-methylmorpholine N-oxide, metal salts, sulfamides, carboxylic acids and amino acids, nitrogenous heterocycles of the imidazole or triazole family, such as imidazole hydrochloride.

Advantageously, the said denaturing agents are chosen from the family of ureas, guanidines, α-hydroxy acid or α-keto acid derivatives, mono-, di, tri- or polyhydroxylated aromatic derivatives, and cyclic or linear amides.

The term "urea", which may be used as hair-relaxing active agent, means any derivative comprising in its chemical formula a carbonyl group simply bonded to two nitrogen atoms. These ureas are more particularly selected from the compounds of general formulae (I) and (II) below:

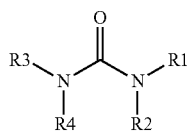

(I)

in which:
R1, R2, R3 and R4 represent, independently:
 (i) a hydrogen atom or
 (ii) a linear or branched C1-C4 lower alkyl or alkenyl radical, optionally substituted with a radical chosen from: hydroxyl, amino, dimethylamino, carboxyl or carboxamide or N-methylcarboxamide,
when R1, R2 and R3 represent a hydrogen atom, R4 may also denote a radical chosen from: carboxamide; methoxy; ethoxy; 1,2,4-triazolyl; cyclopentyl; methoxy-carbonyl; ethoxycarbonyl; CO—CH═CH—COOH; phenyl optionally substituted with a chlorine atom or a hydroxyl radical; benzyl; or 2,5-dioxo-4-imidazolidinyl,
when R1 and R3 represent a hydrogen atom, R2 may also represent a hydrogen atom or a methyl or ethyl radical and R4 an acetyl radical,
when R1=R2=H, R3 and R4 may also form, with the nitrogen atom that bears them, a piperidine or 3-methylpyrazole or 3,5-dimethylpyrazole or maleimide ring, and finally, R1 and R2 and also R3 and R4 may also form, with the nitrogen atom that bears them, an imidazole ring.

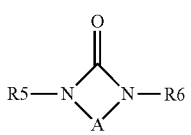

(II)

in which:
R5 and R6 represent, independently of each other:
 (i) a hydrogen atom or
 (ii) a linear or branched C1-C4 lower alkyl radical, optionally substituted with a radical chosen from: hydroxyl, amino, dimethylamino, carboxyl and carboxamide, and
A represents the radicals: CH2-CH2 or CH═CH or CH2-CO or CO—NH or CH═N or CO—CO or CHOH—CHOH or (HOOC)CH—CH or CHOH—CO or CH2-CH2-CH2 or CH2-NH—CO or CH═C(CH3)-CO or NH—CO—NH or CH2-CH2-CO or CH2-N(CH3)-CH2 or NH—CH2-NH or CO—CH(CH3)-CH2 or CO—CH2-CO or CO—NH—CO or CO—CH(COOH)—CH2 or CO—CH═C(COOH) or CO—CH═C(CH3) or CO—C(NH2)═CH or CO—C(CH3)═N or CO—CH═CH or CO—CH═N or CO—N═CH.

Among the compounds of formula (I), mention may be made especially of the following preferred compounds:
urea
methylurea
ethylurea
propylurea
isopropylurea
n-butylurea
sec-butylurea
isobutylurea
tert-butylurea
cyclopentylurea
1-ethoxyurea
2-hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleimide
biuret
N-carbamoylmaleamic acid
1-piperidinecarboxamide
1,2,4-triazol-4-ylurea
hydantoic acid
methyl allophanate
ethyl allophanate
acetylurea
2-hydroxyethyleneurea
2-(hydroxyethyl)ethyleneurea
N-allyl-N'-ethylurea
diallylurea
2-chloroethylurea
N,N-dimethylurea
N,N-diethylurea
N,N-dipropylurea
1-cyclopentyl-1-methylurea
1,3-dimethylurea
1,3-diethylurea
1,3-bis(2-hydroxethyl)urea
1,3,bis(2-hydroxypropyl)urea
1,3-bis(3-hydroxypropyl)urea
1,3-dipropylurea
1-ethyl-3-propylurea
1-sec-butyl-3-methylylurea
1-isobutyl-3-methylurea
1-cyclopentyl-3-methylurea
N-acetyl-N'-methylurea
trimethylurea
1-butyl-3,3-dimethylurea
tetramethylurea
benzylurea.

Among the compounds of formula (II), mention may be made especially of the following preferred compounds:
parabanic acid
1,2-dihydro-3-H-1,2,4-triazol-2-one
barbituric acid
uracil
1-methyluracil
3-methyluracil
5-methyluracil
1,3-dimethyluracil
5-azauracil
6-azauracil 5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidione hydrate
1-methyl-2-imidazolidinone
1,3-dimethyl-2-imidazolidinone
4,5-dihydroxyimidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydrantoin
5-n-propylhydantoin
5-ethyl-5-methylhydantoin
5-hydroxy-5-methylhydantoin
5-hydroxymethylhydantoin
1-allylhydantoin
1-aminohydantoin
hydantoin 5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
barbituric acid
1,3-dimethylbarbituric acid
cyanuric acid
1-methylhexahydropyrimidine-2,4-dione
1,3-dimethyl-3,4,5,6-tetrahydro-2-1H-pyrimidinone
5-(hydroxymethyl-2,4-(1H,3H)-pyrimidinedione
2,4-dihydroxypyrimidine-5-carboxylic acid
6-azathymine
5-methyl-1,3,5-triazinan-2-one
N-carbamoylmaleamic acid
alloxan monohydrate.

Among the compounds of formula (I), mention may be made especially of the following particularly preferred compounds:
urea
methylurea
ethylurea
propylurea
1-ethoxyurea
2-hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
N-carbamoylmaleimide
N-carbamoylmaleamic acid
1-piperidinecarboxamide
1,2,4-triazol-4-ylurea
hydantoic acid
acetylurea
2-hydroxyethyleneurea
2-(hydroxyethyl)ethyleneurea
N-allyl-N'-ethylurea
diallylurea
2-chloroethylurea
N,N-dimethylurea
1,3-dimethylurea
1,3-diethylurea
1,3-bis(2-hydroxyethyl)urea
1,3-dipropylurea
1-ethyl-3-propylurea
N-acetyl-N'-methylurea
benzylurea.

Among the compounds of formula (II) mention made be made especially of the following particularly preferred compounds:
1,2-dihdryo-3-H-1,2,4-traizol-2-one
uracil
1-methyl-2-imidazolidinone
1,3-dimethyl-2-imidazolidinone
4,5-dihydroxyimidazolidin-2-one
1-(2-hydroxyethyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
hydantoin
5-hydroxymethylhydantoin
hydantoin 5-acetic acid
urazole
orotic acid
dihydroxyorotic acid
2,4,5-trihydroxypyrimidine
4,5-diamino-2,6-dihydroxypyrimidine
2,4-dihydroxypyrimidine-5-carboxylic acid
5-methyl-1,3,5-triazinan-2-one
1,3-dimethyl-3,4,5,6-tetrahydro-2-1H-pyrimidinone
N-carbamoylmaleamic acid
alloxan monohydrate.

The term "guanidine", which may be used as relaxing active agent, means any derivative comprising in its chemical formula at least one carbon atom doubly bonded to a nitrogen atom and singly bonded to two other nitrogen atoms. These guanidines are more particularly selected from the compounds of general formula (III) below:

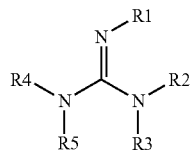 (III)

in which
R1, R2, R3, R4 and R5 represent, independently:
- (iii) a hydrogen atom or
- (iv) a linear or branched C1-C4 lower alkyl or alkenyl radical, optionally substituted with one or two radicals chosen from: hydroxyl, amino, dimethylamino, methoxy, ethoxy, carboxyl, carboxamide, N-methylcarboxamide or $SO_3H$,
  - when R1, R2 and R3 and R4 represent a hydrogen atom, R5 may also denote a radical chosen from the following: acetyl; chloroacetyl; carboxamide; methoxy; ethoxy; 1,2,4-triazolyl; cyclopentyl; methoxycarbonyl; ethoxycarbonyl; CO—CH=CH—COOH; phenyl optionally substituted with a chlorine atom or a hydroxyl radical; benzyl; thiazolidone; benzimidazole; benzoxazole; benzothiazole; or C(=NH)—NR6R7 in which R6 and R7 denote, independently of each other, a hydrogen atom or a linear or branched C1-C4 lower alkyl radical, optionally substituted with one or two radicals chosen from: hydroxyl, amino, dimethylamino, carboxyl or carboxamide; or N-methylcarboxamide; or alternatively a phenyl radical,
  - when R1=R2=R3=H, R4 and R5 may also form, with the nitrogen atom that bears them, a pyrrolidine, piperidine, pyrazole or 1,2,4-triazole ring optionally substituted with one or two radicals chosen from: hydroxyl, amino or carboxyl,
  - when R1=R2=H and R4=H or methyl, R3 and R5 may also together form a 5-membered ring optionally containing an oxo group,
  - and the organic or mineral salts thereof.

Among the compounds of formula (III), mention may be made especially of the following preferred compounds:
guanidine hydrochloride
guanidine acetate
guanidine sulfate
guanidine carbonate
guanidine bicarbonate
guanidine phosphate
guanidine sulfamate
aminoguanidine
aminoguanidine hydrochloride
aminoguanidine sulfate
aminoguanidine bicarbonate
1,3-diaminoguanidine hydrochloride
1-acetylguanidine
chloroacetylguanidine hydrochloride
guanylurea
guanylurea phosphate
phenylguanidine carbonate
phenylguanidine bicarbonate
1-methylguanidine hydrochloride
1,1-dimethylguanidine hydrochloride
1-ethylguanidine hydrochloride
1,1-diethylguanidine hydrochloride
creatine
creatine monohydrate
creatinine hydrochloride
agmatine
agmatine sulfate
guanidinoacetic acid
guanidinosuccinic acid
3-guanidinopropionic acid
4-guanidinobutyric acid
5-guanidinovaleric acid
β-N-methylguanidinopropionic acid
N-methylguanidinopropionic acid
N-(2-hydroxyethyl)guanidine
N-(3-hydroxypropyl)guanidine
biguanide hydrochloride
N-methylbiguanide hydrochloride
N-ethylbiguanide hydrochloride
N-propylbiguanide hydrochloride
N-butylbiguanide hydrochloride
N-butylbiguanide hydrochloride
1,1-dimethylbiguanide hydrochloride
1-phenylbiguanide
1,1,3,3-tetramethylguanidine hydrochloride
1-phenylbiguanide
1,1,3,3-tetramethylguanidine hydrochloride
2-tert-butyl-1,1,3,3-tetramethylguanidine hydrochloride
L-arginine
D-arginine
DL-arginine
arginic acid
N-amidino-N-(2,3-dihydroxypropyl)glycine
N-amidinotaurine
2-imino-2-imidazolidineacetic acid
1-(2,2-diethoxyethyl)guanidine
1H-pyrazole-1-carboxamidine hydrochloride
5-hydroxy-3-methyl-1H-pyrazole-1-carbox-imidamide
3,5-diamino-1H-1,2,4-triazole-1-carboximidamide hydrochloride
2-guanidone-4-thiazolidone
2-guanidinobenzimidazole
2-guanidinobenzoxazole
2-guanidinobenzothiazole
pyrrolidinoformamidine hydrochloride.

Among the compounds of formula (III), mention may be made especially of the following particularly preferred compounds:
guanidine hydrochloride
guanidine acetate
guanidine sulfate
guanidine carbonate
guanidine bicarbonate
guanidine phosphate
guanidine sulfamate
aminoguanidine hydrochloride
aminoguanidine sulfate
aminoguanidine bicarbonate
1,3-diaminoguanidine hydrochloride
guanylurea phosphate
1-methylguanidine hydrochloride
1,1-dimethylguanidine hydrochloride
1-ethylguanidine hydrochloride
creatine monohydrate
creatinine hydrochloride
agmatine
agmatine sulfate
guanidinoacetic acid
guanidinosuccinic acid
3-guanidinopropionic acid
β-N-methylguanidinopropionic acid
N-methylguanidinopropionic acid N-(2-hydroxyethyl)guanidine
N-(3-hydroxypropyl)guanidine
biguanide hydrochloride
N-methylbiguanide hydrochloride
N-ethylbiguanide hydrochloride
1,1-dimethylbiguanide hydrochloride
1,1,3,3-tetramethylguanidine hydrochloride
2-tert-butyl-1,1,3,3-tetramethylguanidine hydrochloride
L-arginine
DL-arginine
arginic acid
N-amidino-N-(2,3-dihydroxypropyl)glycine
N-amidinotaurine
2-imino-1-imidazolidineacetic acid
1H-pyrazole-1-carboxamidine hydrochloride
3,5-diamino-1H-1,2,4-triazole-1-carboximidamide hydrochloride
2-guanidone-4-thiazolidone.

The term "α-hydroxy acid and α-keto acid derivatives", which may be used as hair-relaxing active agent, means any derivative selected from the compounds of general formulae (IV) and (V) below:

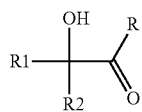

(IV)

R1 represents H, OH, NH2, CH2-COOH or a linear or branched C1-C4 alkyl radical,
R2 represents H, COOH, CHOH—COOH, CF3, CH=CH2, NHCONH2, a linear, branched or cyclic C1-C8 alkyl radical optionally substituted with a radical chosen from OH, Cl, NH2, COOH, CF3 and SCH3; or a phenyl or benzyl radical optionally substituted with one OH or OCH3 radical;
or alternatively the radical

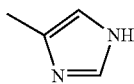

R1 and R2 may also together form an oxo radical (=O) or a cyclopropyl, cyclobutyl, hydroxycyclobutyl, cyclo pentyl or cyclohexyl ring with the carbon atom that bears them, or alternatively a radical

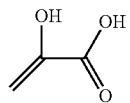

when R1=H, R2 may also represent a (CHOH)2CH2OH or (CHOH)3CH2OH radical,
R represents OH or NR3R4 with R3, R4=H or a linear or branched C1-C4 alkyl radical optionally substituted with one or two OH radicals
and the stereoisomers, organic or mineral salts and solvates thereof.

Preferred compounds of formula (IV) that may be mentioned include:
glycolic acid
oxalic acid
lactic acid
1-hydroxy-1-cyclopropanecarboxylic acid
2-hydroxy-3-butenoic acid
2-hydroxyisobutyric acid
2-hydroxy-n-butyric acid
isoserine
glyceric acid
2-hydroxy-3-methylbutyric acid
2-hydroxy-2-methylbutyric acid
2-hydroxyvaleric acid
4-amino-2-hydroxybutyric acid
1-hydroxycyclohexanecarboxylic acid
dihydroxyfumaric acid
citramalic acid
tartaric acid
citric acid
2-hydroxy-4-(methylthio)butyric acid
mandelic acid
2-hydroxy-3-methylvaleric acid
glyoxylurea
β-imidazolelactic acid
2-trifluoromethyl-2-hydroxypropionic acid
hexahydromandelic acid
2-hydroxyoctanoic acid
arabic acid
3-phenyllactic acid
hydroxyphenylglycine
3-hydroxymandelic acid
4-hydroxymandelic acid
2-hydroxynonanoic acid
L-arginic acid
3-methoxymandelic acid
4-methoxymandelic acid
3-(4-hydroxyphenyl)lactic acid
tartronic acid
tartaric acid
β-chlorolactic acid
1-cyclopentanol-1-carboxylic acid
1,2-dihydroxycyclobutanecarboxylic acid
2-ethyl-2-hydroxybutric acid
α-hydroxyisocaproic acid
α-hydroxycaproic acid
2-hydroxy-3,3-dimethylbutyric acid
malic acid
hydroxytartronic acid
gluconic acid
lactamide
N-methyllactamide
N-ethyllactamide
N,N-dimethyllactamide
N-2-hydroxyethyllactamide
and the stereoisomers, organic or mineral salts and solvates thereof.

The compounds of formula (IV) that are particularly preferred are chosen from:
glycolic acid
oxalic acid
L-lactic acid
DL-lactic acid
D-lactic acid
malic acid
tartaric acid
DL-glyceric acid
arabic acid
gluconic acid
hydroxytartronic acid
lactamide N-methyllactamide
N-ethyllactamide
N-2-hydroxyethyllactamide Definition of the α-keto acid derivatives of general formula (V):

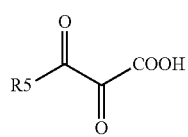

R5 represents COOH, a linear or branched C1-C6 alkyl radical optionally substituted with an OH, COOH or Br radical; a phenyl or benzyl radical optionally substituted with an OH or COOH radical; or an indolyl radical or

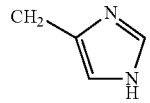

and the stereoisomers, organic or mineral salts and solvates thereof.

The preferred compounds of formula (V) are chosen from:
pyruvic acid
2-ketobutyric acid
β-hydroxypyruvic acid
3-methyl-2-oxobutyric acid
2-oxovaleric acid
ketomalonic acid
3-methyl-2-oxovaleric acid
trimethylpyruvic acid
oxolacetic acid
2-ketoglutaric acid
benzylformic acid
2-oxooctanoic acid
2-oxoadipic acid
phenylpyruvic acid
bromopyruvic acid
2-ketopimelic acid
4-hydroxyphenylpyruvic acid
3-indoleglyoxalic acid
imidazolopyruvic acid HCl
2-keto-L-gulonic acid
2-carboxy-α-oxobenzeneacetic acid
3-indolepyruvic acid
2-ketoglutaric acid dihydrate
pyruvamide
N-methylpyruvamide
N-ethylpyruvamide
N,N-dimethylpyruvamide
N-2-hydroxyethylpyruvamide
and the stereoisomers, organic or mineral salts and solvates thereof.

The compounds of formula (V) that are particularly preferred are chosen from:
pyruvic acid
2-ketobutyric acid
β-hydroxypyruvic acid
ketomalonic acid
oxolacetic acid
2-ketoglutaric acid
2-keto-L-gulonic acid
2-ketoglutaric acid dihydrate
pyruvamide
and the stereoisomers, organic or mineral salts and solvates thereof.

The term "polyhydroxylated aromatic derivatives", which may be used as hair-relaxing active agent, means any derivative selected from the compounds of general formula (VI) below:

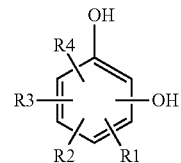

in which:
R1, R2, R3 and R4 represent, independently of each other: H, F, Cl, Br, OH, OCH$_3$, OEt, CHO, COCH$_3$, COOH, CH$_2$NH$_2$, CH$_2$CH$_2$NH$_2$, CH$_2$OH, CH$_2$CH$_2$OH, CH$_2$COCH$_3$, CH$_2$COOH, CH$_2$CH$_2$COOH, CH$_2$CONH$_2$, CHOH—CH$_2$OH, —CH(NH$_2$) COOH, NHCOCH$_3$, COCH$_2$CH$_3$, CONH$_2$
or alternatively a linear or branched C1-C5 alkyl radical when the two OH radicals are in a meta position and when R1, R2 and R3 represent a hydrogen atom, R4 may also represent NH$_2$,
and the stereoisomers, organic or mineral salts and solvates thereof.

The preferred compounds of formula (VI) are chosen from:
catechol
resorcinol
4-methylcatechol
3-methylcatechol
2-methylresorcinol
5-methylresorcinol
4-methylresorcinol
pyrogallol
1,2,4-trihydroxybenzene
phloroglucinol
3-fluorocatechol
4-fluorocatechol
4-fluororesorcinol
2,3-dihydroxybenzaldehyde
3,4-dihydroxybenzaldehyde
2,4-dihydroxybenzaldehyde
3,5-dihydroxybenzaldehyde
4-ethylcatechol
4-ethyl resorcinol
2,5-dimethylresorcinol
4,5-dimethylresorcinol
2,4-dimethyl-1,3-benzenediol
3,4-dihydroxybenzylamine
3,5-dihydroxybenzylamine
3-methoxycatechol
5-methylpyrogallol
3,4-dihydroxybenzyl alcohol
5-methoxyresorcinol
2,4,6-trihydroxytoluene
3,5-dihydroxybenzyl alcohol
2-methoxyresorcinol
5-methylpyrogallol
4-methoxyresorcinol 3,5-dihydroxytoluene monohydrate
4-chlorocatechol
3-chlorocatechol
4-chlororesorcinol
2-chlororesorcinol
3',4'-dihydroxyacetophenone
2',3'-dihydroxyacetophenone
2',6'-dihydroxyacetophenone
2',4'-dihydroxyacetophenone
3',5'-dihydroxyacetophenone
2,6-dihydroxy-4-methylbenzaldehyde
3-isopropylcatechol
4-isopropylcatechol
4-propylresorcinol
2,4-dihydroxy-1,3,5-trimethylbenzene
3,4-dihydroxybenzamide
3,5-dihydroxybenzamide
2,6-dihydroxybenzamide
2,4-dihydroxybenzamide
3-hydroxytyramine
2,3-dihydroxybenzoic acid
3,4-dihydroxybenzoic acid
2,4-dihydroxybenzoic acid
2,6-dihydroxybenzoic acid
3,5-dihydroxybenzoic acid
2,3,4-trihydroxybenzaldehyde
2,4,6-trihydroxybenzaldehyde
3,4,5-trihydroxybenzaldehyde
2,4,5-trihydroxybenzaldehyde
2-(3,4-dihydroxyphenyl)ethanol
2,4,6-trihydroxy-1,3-dimethylbenzene
2,6-dihydroxy-4-methylbenzyl alcohol
2-fluoro-3,4-dihydroxybenzaldehyde
3,4-dihydroxy-6-fluorobenzaldehyde
2-methoxyphloroglucinol
3,5-dihydroxyanisole hydrate
4-aminoresorcinol hydrochloride
2-aminoresorcinol hydrochloride
5-aminobenzene-1,3-diol hydrochloride
phloroglucinol dihydrate
3',4'-dihydroxypropiophenone
3,4-dihydroxyphenylacetone
(2,3-dihydroxyphenyl)acetone
2',4'-dihydroxypropiophenone
2',4'-dihydroxy-3'-methylacetophenone
(2,4-dihydroxyphenyl)acetone
(3,5-dihydroxyphenyl)acetone
2,6-dihydroxy-4'-methylacetophenone
4-tert-butylcatechol
4-N-butylresorcinol
2,4-diethyl-1,3-benzenediol
3,4-dihydroxyphenylacetamide
3-hydroxyacetaminophen
2',3',4'-trihydroxyacetophenone
3,4-dihydroxyphenylacetic acid
2,3-dihydroxy-4-methoxybenzaldehyde
3,4-dihydroxy-5-methoxybenzaldehyde
2',3',4'-trihydroxyacetophenone
2',4',6'-trihydroxyacetophenone
3,5-dihydroxy-4-methylbenzoic acid
2,6-dihydroxy-4-methylbenzoic acid
2,4-dihydroxy-6-methylbenzoic acid
3,5-dihydroxyphenylacetic acid
2-ethyl-5-methoxybenzene-1,3-diol
3,4,5,-trihydroxybenzamide
4-amino-3,5-dihydroxybenzoic acid
2,3,4-trihydroxybenzoic acid
2,3,4-trihydroxybenzoic acid
gallic acid
2,4,6-trihydroxybenzoic acid
3,4-dihydroxyphenyl glycol
1,2-dihydroxy-4,5-dimethoxybenzene
3,5-dihydroxyacetophenone monohydrate
3,4-dihydroxybenzoic acid monohydrate
3,4,5-trihydroxybenzaldehyde
hexahydroxybenzene
3,5-dihydroxybenzylamine hydrochloride
4,6-diaminoresorcinol hydrochloride
4,5-dichlorocatechol
3,5-dichlorocatechol
4,6-dichlororesorcinol
2',4'-dihydroxy-3'-methylpropiophenone
1-(3-ethyl-2,6-dihydroxyphenyl)ethan-1-one
3-(3,4-dihydroxyphenyl)propionic acid
(2,3,4-trihydroxyphenyl)acetone
(2,4,5-trihydroxyphenyl)acetone
(3,4,5-trihydroxyphenyl)acetone
2',6'-dihydroxy-4'-methoxyacetophenone
1-(2,6-dihydroxy-3-methoxyphenyl)ethan-1-one
3(2,4-dihydroxyphenylpropionic acid
2,4-dihydroxy-3,6-dimethylbenzoic acid
(2,3,4-trihydroxyphenyl)acetone
(2,4,5-trihydroxyphenyl)acetone
(2,4,6-trihydroxyphenyl)acetone
(3,4,5-trihydroxyphenyl)acetone
3,4-dihydroxymandelic acid
5-hydroxyisovanillic acid
3,4,5-trihydroxybenzamide hydrate
4-bromocatechol
and the stereoisomers, organic or mineral salts and solvates thereof.

The compounds of formula (VI) that are particularly preferred are chosen from:
resorcinol
2-methylresorcinol
5-methyl resorcinol
4-methylresorcinol
pyrogallol
1,2,4-trihydroxybenzene
4-ethylresorcinol
2,5-dimethylresorcinol
4,5-dimethylresorcinol
2,4-dimethyl-1,3-benzenediol
3,4-dihydroxybenzylamine
3,5-dihydroxybenzylamine
5-methylpyrogallol
3,4-dihydroxybenzyl alcohol
5-methoxyresorcinol
2,4,6-trihydroxytoluene
3,5-dihydroxybenzyl alcohol
2-methoxyresorcinol
5-methylpyrogallol
4-methoxyresorcinol
3,5-dihydroxytoluene monohydrate
4-propylresorcinol
2,4-dihydroxy-1,3,5-trimethylbenzene
3,4-dihydroxybenzamide
3,5-dihydroxybenzamide
2,6-dihydroxybenzamide
2,4-dihydroxybenzamide
3-hydroxytyramine
2,3-dihydroxybenzoic acid
3,4-dihydroxybenzoic acid
2,6-dihydroxybenzoic acid 3,5-dihydroxybenzoic acid
2-(3,4-dihydroxyphenyl)ethanol
2,4,6-trihydroxy-1,3-dimethylbenzene
2,6-dihydroxy-4-methylbenzyl alcohol
2-methoxyphloroglucinol
3,5-dihydroxyanisole hydrate
4-aminoresorcinol hydrochloride
2-aminoresorcinol hydrochloride
5-aminobenzene-1,3-diol hydrochloride
phloroglucinol dihydrate
2,4-diethyl-1,3-benzenediol
3,4-dihydroxyphenylacetamide
3,4-dihydroxyphenylacetic acid
3,5-dihydroxy-4-methylbenzoic acid
2,6-dihydroxy-4-methylbenzoic acid
2,4-dihydroxy-6-methylbenzoic acid
3,5-dihydroxyphenylacetic acid
2-ethyl-5-methoxybenzene-1,3-diol
3,4,5-trihydroxybenzamide
4-amino-3,5-dihydroxybenzoic acid
3,4-trihydroxybenzoic acid
gallic acid
2,4,6-trihydroxybenzoic acid
DL-3,4-dihydroxyphenyl glycol
1,2-dihydroxy-4,5-dimethoxybenzene
3,4-dihydroxybenzoic acid monohydrate
hexahydroxybenzene
3,5-dihydroxybenzylamine hydrochloride
sodium γ-resorcylate
sodium β-resorcylate
4,6-diaminoresorcinol hydrochloride
3-(3,4-dihydroxyphenyl)propionic acid
2,4-dihydroxy-3,6-dimethylbenzoic acid
DL-3,4-dihydroxymandelic acid
hydroxyisovanillic acid
3,4,5-trihydroxybenzamide acid hydrate
gallic acid monohydrate
and the stereoisomers, organic or mineral salts and solvates thereof.

The term "cyclic and linear amide derivatives" which may be used as hair-relaxing active agent, means any derivative selected from the compounds of general formulae (VII) and (VIII) below:

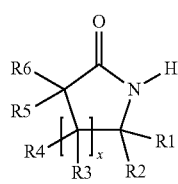

(VII)

with
X=0 to 3
R1, R2, R3, R4, R5 and R6, which may be identical or different, possibly taking the following meaning:
  H,
  F,
  linear or branched C1-C30 alkyl, possibly comprising one or more unsaturations,
    optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
    optionally substituted with —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —OSO2R7, —C(S)NR7R8, —NR7C(S)R8, an aromatic or non-aromatic, heterocyclic or non-heterocyclic ring, possibly containing 3 to 10 atoms,
  —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —C(S)NR7R8, —NR7C(S)R8,
  an aromatic or non-aromatic, heterocyclic or non-heterocyclic ring, possibly containing 3 to 10 carbon atoms, which is optionally substituted,
  R1, R2, R3, R4, R5 and R6 possibly forming in pairs, with the carbon atoms to which they are attached, a (hetero)cycle of 3 to 7 atoms, optionally interrupted with O, S, N, —C(O)—, —C(O)O—, —C(O)NR7-,
  R1R2, R3R4, and R5R6 possibly being combined in pairs to form an oxo function,
R7, R8 and R9, which may be identical or different, possibly taking the following meaning:
  H, F, optionally substituted linear or branched C1-C30 alkyl, possibly containing one or more unsaturations,
  one of the 20 natural N-branched amino acids, C-protected with standard protecting groups or one of the 20 natural C-branched amino acids, N-protected with standard protecting groups,
  an aromatic or non-aromatic, heterocyclic or non-heterocyclic ring, possibly containing 3 to 10 atoms,
and also the stereoisomers, organic or mineral salts and solvates thereof.

The preferred compounds of formula (VII) are chosen from:
2-pyrrolidone
3-methyl-2-pyrrolidone
pyroglutamic acid
5-methyl-2-pyrrolidone
succinimide
α-methyl-α-phenylsuccinimide
ethyl pyroglutamate
2-oxo-4-phenylpyrrolidine-3-carboxylic acid
pyrrolidonyl-4-butyramide
5-(hydroxymethyl)-2-pyrrolidinone
methyl pyroglutamate
ethyl 2-oxo-4-phenyl-3-pyrrolidinecarboxylate
4-(hydroxy)-4-methylpyrrolidin-2-one
4-fluoro-5-pyrrolidone-2-carboxylic acid
4,4-pentamethylene-2-pyrrolidinone
[(5-oxopyrrolidine-2-carbonyl)amino]acetic acid
2-[(5-oxopyrrolidine-2-carbonyl)amino]-3-phenylpropionic acid
5-methoxy-2-pyrrolidinone
2-azabicyclo[2.2.1]hept-5-en-3-one
butyl 2-pyrrolidone-5-carboxylate
octyl 2-pyrrolidone-5-carboxylate
4-carbamoyl-2-[(5-oxopyrrolidin-2-carbonyl)amino]-butyric acid
4-hydroxy-2-pyrrolidinone
2-dimethylamino ethyl 5-oxopyrrolidine-2-carboxylate
3-(1H-indol-3-yl)-2-[(5-oxopyrrolidin-2-carbonyl)-amino] propionic acid 5-pyridin-3-ylpyrrolidin-2-one
2-azabicyclo[2.2.1]heptan-3-one
methyl 2-[3-(methoxymethyl)-5-oxo-2-pyrrolidinyl]-acetate
4-phenyl-2-pyrrolidinone
4-spiro-[3[(2-pyrrolidonone)]piperidine
(4-[3-(cyclopentyloxy)-4-methoxyphenyl]pyrrolidin-2-one
2-amino-5-oxo-5-(5-oxopyrrolidin-2-yl)pentanoic acid
2-(2,5-dioxopyrrolidin-3-ylsulfanyl)nicotinic acid
3-hydroxynorcotinine
3-benzyl-5-hydroxymethylpyrrolin-2-one
ethyl 4-methylpyroglutamate
ethyl 4-ethylpyroglutamate
ethyl 4-isopropylpyroglutamate
ethyl 4-benzylpyroglutamate
3-ethyl-5-hydroxymethylpyrrolidin-2-one
5-hydroxymethyl-3-methylpyrrolidin-2-one
5-oxopyrrolidine-3-carboxylic acid
5-hydroxymethyl-3-isopropylpyrrolidin-2-one
5-hydroxymethylpyrrolidin-2-one
5-aminomethylpyrrolidin-2-one
ethyl 2-oxopyrrolidine-3-carboxylate
3-hydroxypyrrolidin-2-one
3-ethyl-4-methylpyrroline-2-one
3,4-(1,3-propanediyl)-2-pyrrolidinone
δ-valerolactam
3-carbethoxy-2-piperidone
glutarimide
3,3-dimethylglutarimide
3-ethyl-3-methylglutarimide
6-methyl-2-piperidone
3-methylpiperidin-2-one
D-mannono-D-lactam
N-(2-aminoethyl)-2-oxopiperidine-3-carboxamide
4-phenyl-δ-valerolactam
3-amino-4-phenyl-δ-valerolactam
4-methyl-3-phenyl-δ-valerolactam
3-methyl-5-phenyl-δ-valerolactam
3-(2-isopropoxycarbonylethyl)-6-oxopiperidine-3-carboxylic acid
3-(2-benzylcarbamoylethyl)-6-oxopioperidine-3-carboxylic acid
methyl-2-oxopiperidine-3-carboxylate
3,4,5-trihydroxy-6-oxo-2-piperidinecarboxylic acid
2-piperidinone-6-carboxylic acid
5-hydroxypiperidin-2-one
ethyl 5-methyl-2-oxo-3-piperidinecarboxylate
6-oxopiperidine-2-carboxylic acid
4-hydroxypiperidin-2-one
2-azetidinone
ε-caprolactam
and the stereoisomers, organic or mineral salts and/or solvates thereof.

The compounds of formula (VII) that are particularly preferred are chosen from:
2-pyrrolidone
pyroglutamic acid
3-methyl-2-pyrrolidone
5-methyl-2-pyrrolidone
5-(hydroxymethyl)-2-pyrrolidinone
5-oxopyrrolidine-3-carboxylic acid
5-aminomethylpyrrolidin-2-one
4-hydroxy-2-pyrrolidinone
and the stereoisomers, organic or mineral salts and/or solvates thereof.

Definition of the linear amides of general formula (VIII)

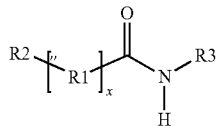

(VIII)

with
X=0 or 1;
if X=0
R2 possibly taking the following meaning:
  H
  F, Cl
  an optionally substituted, heterocyclic or non-heterocyclic, aromatic or non-aromatic ring, which may contain 3 to 10 atoms,
  —OR7, —SR7, —C(O)R7, —OC(O)R7, —C(O)OR7, —C(O)NR7R8, —OC(O)NR7R8, —SO₂NR7R8, —C(S)NR7R8,
R3 possibly taking the following meaning:
  H, except if R2 is 3-pyridine
  linear or branched C1-C30 alkyl, possibly comprising one or more unsaturations,
    optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
    optionally substituted with:
      F, Cl
      —OR7, —SR7, —NR7R8, —C(O)R7, —OC(O)R7, —C(O)OR7, —C(O)NR7R8, —NR7C(O)R8, —OC(O)NR7R8, —NR7C(O)ORB, —NR7C(O)NR8R9, —NR7SO2R8, —NR7SO2NR8R9, —SO2NR7R8, —OSO2R7, —C(S)NR7R8, —NR7C(S)R8
    a heterocyclic or non-heterocyclic, aromatic or non-aromatic ring, possibly containing 3 to 10 atoms,
R7, R8 and R9, which may be identical or different, possibly taking the following meaning:
  H,
  linear or branched C1-C30 alkyl, possibly comprising one or more unsaturations,
  one of the 20 natural N-branched amino acids, C-protected with standard protecting groups, or one of the 20 natural C-branched amino acids, N-protected with standard protecting groups,
  a heterocyclic or non-heterocyclic, aromatic or non-aromatic ring, possibly containing 3 to 10 atoms,
if X=1
R1 possibly taking the following meaning:
  linear or branched C1-C30 alkylene, possibly containing one or more unsaturations,
    optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, —NR7SO2NR8-, —SO2NR7-, —OSO2-, —C(S)NR7-, —NR7C(S)—,
    optionally substituted with:
      F, Cl
      —OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)

NR8R9, —NR7SO2R8, —NR7SO2NR8R9,
—SO2NR7R8, —OSO2R7, —C(S)NR7R8,
—NR7C(S)R8,
an aromatic or non-aromatic, heterocyclic or non-heterocyclic ring, possibly containing 3 to 10 atoms, with the exception of hydroxyl or oxo substituents in a position alpha to the amide function R2 possibly taking the following meaning:
H
F, Cl
an aromatic or non-aromatic, heterocyclic or non-heterocyclic ring, which is optionally substituted, possibly containing 3 to 10 atoms,
—OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —C(S)NR7R8, —NR7C(S)R8

R3 possibly taking the following meaning:
H
linear or branched C1-C30 alkyl, possibly containing one or more unsaturations,
optionally interrupted with —O—, —S—, —NR7-, —C(O)—, —OC(O)—, —C(O)O—, —C(O)NR7-, —NR7C(O)—, —OC(O)NR7-, —NR7C(O)O—, —NR7C(O)NR8-, —NR7SO2-, NR7SO2NR8-, —SO2NR7-, —OSO2-, —C(S)NR7-, —NR7C(S)—,
optionally substituted with:
F, Cl
—OR7, —SR7, —NR7R8, —C(O)R7, —OC(O)R7, —C(O)OR7, —C(O)NR7R8, —NR7C(O)R8, —OC(O)NR7R8, —NR7C(O)OR8, —NR7C(O)NR8R9, —NR7SO2R8, —NR7SO2NR8R9, —SO2NR7R8, —OSO2R7, —C(S)NR7R8, —NR7C(S)R8
an aromatic or non-aromatic, heterocyclic or non-heterocyclic ring, possibly containing 3 to 10 atoms, R7, R8 and R9, which may be identical or different, possibly taking the following meaning:
H,
linear or branched C1-C30 alkyl, possibly containing one or more unsaturations,
one of the 20 natural N-branched amino acids, C-protected with standard protecting groups, or one of the 20 natural C-branched amino acids, N-protected with standard protecting groups,
an aromatic or non-aromatic, heterocyclic or non-heterocyclic ring, possibly containing 3 to 10 atoms, if R2(R1)x represents a fatty acid-based saturated or unsaturated alkyl radical, this alkyl radical contains less than 16 carbon atoms,
and also the stereoisomers thereof and the organic or mineral salts and solvates thereof.

Preferably, if R2(R1)x represents a fatty acid-based saturated or unsaturated alkyl radical, this alkyl radical contains fewer than 9 carbon atoms.

The preferred compounds of formula (VIII) are chosen from:
acetamide
N-methylacetamide
propionamide
N-ethylacetamide
N-methylpropionamide
N-butyramide
N-(hydroxymethyl)acetamide
methoxyacetamide
hydracrylamide
2-mercaptoacetamide
acetoacetamide
N—(N-propyl)acetamide
N-ethylpropionamide
valeramide
malonamide
N-acetylethylenediamine
2-amino-N-ethylacetamide
N-acetylethanolamine
3-chloropropionamide
glycinamide
N-(cyclopropylmethyl)acetamide
N-methylacetoacetamide
1-acetamidoacetone
N-methylvaleramide
N-butylacetamide
hexanamide
N-acetylglycinamide
succinamide
N-ethyl-2-methylaminoacetamide
N-acetylglycine
succinamic acid
methylcarbamoylacetate
N-(2-hydroxyethyl)propionamide
N1-(3-hydroxypropyl)acetamide
5-hydroxyvaleramide
3-amino-3-thioxopropanamide
O-(2-hydroxyethyl)glycolamide
3,4-dihydroxybutyramide
N-(2-chloroethyl)acetamide
N-(3-methylbutyl)acetamide
N-methylsuccinamic acid
ethyl carbamoylacetate
glycylglycine
asparagine
2-amino-N-(2-methoxyethyl)acetamide
2-(2-amino-2-oxoethoxy)acetic acid
2-phenylacetamide
pyridine-2-acetamide
pyridine-4-acetamide
methylsulfonylacetamide
4-aminobutyramide
5-acetaminomethyltetrazole
thiphene-2-acetamide
4-thiazoleacetamide
1-aminocyclopentanacetamide
2-piperazin-1-ylacetamide
N-octanamide
N,N'-diacetylethylenediamine
adipamide
2-morpholinoacetamide
ethyl acetamidoacetate
4-acetamidbutyric acid
2-(acetylamino)ethyl acetate
N-(2-hydroxyethyl)acetoacetamide
isopropyl carbamoylacetate
2-amino-N-methylsuccinamic acid
glutamine
N-(2-methoxyethyl)-2-methylaminoacetamide
N-methyl-2-phenylacetamide
N-benzylacetamide
N-propylpyrrolidine-2-carboxamide
N-(tert-butyl)-1,2,3,4-tetrahydroisoquinoline-2-carboxamide
N,N-butylpropionamide N-1,3,3-trimethylbutanamide
N-α-acetyl-L-lysine-N-methylamide
L-proline N-octylamide
and also the stereoisomers thereof and the organic or mineral salts and solvates thereof,
and also the following amino acids and derivatives:
AC-ALA-NHME
AC-β-ALA-OH
AC-β-ALA-OME
AC-GLY-NHME
AC-HIS-NHME
AC-ILE-NHME
AC-LEU-GLY-OH
AC-LEU-NHME
AC-LYS-NHME
AC-PHE-NHME
AC-SER-GLY-OH
AC-VAL-NHME
H-β-ALA-GLY-OH
H-β-ALA-NH2
H-GLY-β-ALA-OH
H-GLY-NHME
H-PRO-ALA-OH
H-PRO-ALA-OH
H-PRO-O-ALA-OH
H-PRO-GLY-NH2
H-PRO-GLY-OH
H-PRO-GLY-OH
H-PRO-ILE-OH
H-PRO-LEU-OH
H-PRO-NHCH3
H-PRO-NHET
H-PRO-SER-OH
H-PRO-VAL-OH
H-PRO-VAL-OH
SAR-GLY-OH
SAR-NH2
and also the stereoisomers thereof and the organic or mineral salts and solvates thereof.

The compounds of formula (VIII) that are particularly preferred are chosen from:
glycinamide
acetamide
N-methylacetamide
N-ethylacetamide
propionamide
N-ethylpropionamide
and also the stereoisomers thereof and the organic or mineral salts and solvates thereof.

In the compositions according to the invention intended for a process of relaxing, uncurling or straightening the hair, the mixture in any proportion of at least two denaturing agents as defined previously is advantageously present in an overall molar concentration of between 1 M and 8 M and more advantageously in a concentration of between 2 M and 8 M.

In the process according to the invention and in the kit, the pH of the compositions is preferably less than 9 and more preferentially less than 7.

The compositions according to the invention are either in the form of an aqueous solution or in the form of a thickened cream so as to keep the hair as straight as possible. These creams are prepared in the form of "heavy" emulsions.

For the purpose of improving the cosmetic properties of keratin fibres or to attenuate or avoid their degradation, the composition used according to the invention may also comprise one or more additional cosmetic active agents. Generally, the said additional cosmetic active agent(s) represent(s) from 0.01% to 30% and preferably from 0.1% to 10% by weight relative to the total weight of the cosmetic composition.

Generally, the composition applied to the keratin fibres is applied in an amount of from 0.05 to 20 g and preferably from 0.1 to 10 g of composition per gram of dry keratin fibre.

After applying the composition, and before raising the temperature of the keratin fibres using a heating means, the said composition may be left to act, generally for 30 seconds to 60 minutes and preferably 5 to 45 minutes.

The process according to the invention includes, after the step of applying the composition, a step of raising the temperature of the keratin fibres, using a heating means, to a temperature of between 110° C. and 250° C.

Advantageously, an iron is used as heating means.

For the purposes of the present invention, the term "iron" means a device for heating keratin fibres that places the said fibres and the heating device in contact, the end of the iron that comes into contact with the hair generally having two flat surfaces. These two flat surfaces may be metallic. They may be smooth or crinkled.

As examples of irons that may be used in the process according to the invention, mention may be made of flat irons of any type, and in particular, in a non-limiting manner, those described in U.S. Pat. No. 5,957,140 and U.S. Pat. No. 5,046,516.

The iron may be applied by successive separate touches of a few seconds, or by gradually moving or sliding it along the locks.

Preferably, in the process according to the invention, the iron is applied by continuous movement from the root to the end, in one or more passes.

The process according to the invention may also include an additional step of partial predrying of the keratin fibres before the step of raising the temperature, so as to avoid substantial evolution of steam that might burn the stylist's hands and the individual's scalp. This predrying step may take place, for example, using a hairdryer, a hood or alternatively by drying in the open air.

The invention especially concerns processes in which the composition comprises at least one of the following combinations:
  at least one denaturing agent is a guanidine corresponding to formula (III) and at least one denaturing agent corresponds to formula (V),
  at least one denaturing agent is a urea corresponding to formula (I) and at least one denaturing agent corresponds to formula (III),
  at least one denaturing agent is a urea corresponding to formula (I) and at least one denaturing agent corresponds to formula (V).

The invention also relates to a kit comprising at least:
  one heating means that affords a temperature of between 110 and 250° C.,
  one hair-relaxing composition containing at least two denaturing agents.

The invention also relates to a kit comprising at least:
  one heating means that affords a temperature of between 110 and 250° C.,
  a first hair-relaxing composition containing at least one denaturing agent,
  a second hair-relaxing composition containing at least one denaturing agent.

The invention may be understood more clearly with the aid of the non-limiting examples that follow, which constitute preferential embodiments of the compositions according to the invention.

The compositions may be applied as a mixture (see Example 1 and 2) or successively (see Example 3).

EXAMPLE 1

A simplified hair-relaxing composition is prepared, containing a mixture of guanidine hydrochloride at a concentration of 2 M and of pyruvic acid at concentration of 2 M, in water, as hair-relaxing active agent. This composition is applied to naturally curly African hair for 15 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

EXAMPLE 2

A simplified hair-relaxing composition is prepared, containing a mixture of guanidine hydrochloride at a concentration of 4 M and of urea at a concentration of 4 M, in water, as hair-relaxing active agent. This composition is applied to naturally curly African hair for 15 minutes at a temperature of 40° C., and the hair is then rapidly towel-dried.

Lock-by-lock straightening of the head of hair is then performed using a flat iron heated to 180° C., for 10 to 15 seconds. The hair is efficiently relaxed and feels soft.

EXAMPLE 3

A simplified hair-relaxing composition is prepared, containing urea at a concentration of 2 M in water, as hair-relaxing active agent. This composition is applied to naturally curly African hair for 15 minutes at a temperature of 40° C., and the hair is then rapidly towel-dried. A second simplified hair-relaxing composition is prepared, containing pyruvic acid at a concentration of 2 M, in water, as hair-relaxing active agent. This composition is applied to the same hair for 15 minutes at a temperature of 40° C., and the hair is then rapidly towel-dried. Lock-by-lock straightening of the head of hair is then performed using a flat iron heated to 180° C., for 10 to 15 seconds. The hair is efficiently relaxed and feels soft.

The invention claimed is:

1. A process for relaxing keratin fibres, comprising:
   (i) applying to the keratin fibres a hair-relaxing composition containing at least two denaturing agents chosen from:
      (a) ureas of formula (I):

$$R3\text{-}N(R4)\text{-}C(=O)\text{-}N(R2)\text{-}R1 \quad (I)$$

in which R1, R2, R3 and R4 are independently chosen from:
   a hydrogen atom, and
   linear or branched C1-C4 lower alkyl or alkenyl radicals, optionally substituted with a radical chosen from hydroxyl, amino, and dimethylamino radicals, and
      (b) α-hydroxy acid derivatives of formula (IV):

$$R1\text{-}C(OH)(R2)\text{-}C(=O)\text{-}R \quad (IV)$$

in which:
   R is chosen from OH and NR3R4, wherein R3 and R4 are independently chosen from hydrogen and linear or branched C1-C4 alkyl radicals optionally substituted with at least one OH radical;
   R1 is chosen from H, OH, NH2, CH2-COOH, and linear or branched C1-C4 alkyl radicals,
   R2 is chosen from:
      H, COOH, CHOH—COOH, CF3, CH=CH2, NHCONH2,
      linear, branched or cyclic C1-C8 alkyl radicals optionally substituted with a radical chosen from OH, Cl, NH2, COOH, CF3, and SCH3;
      phenyl and benzyl radicals optionally substituted with an OH or OCH3 radical; and
      the radical (4-methylimidazole radical structure)

R1 and R2 may optionally form together an oxo radical (=O) or a cyclopropyl, cyclobutyl, hydroxycyclobutyl, cyclopentyl or cyclohexyl ring with the carbon atom that bears them, and
   when R1 is H, then R2 may also be chosen from (CHOH)2CH2OH and (CHOH)3CH2OH,
   or alternatively the α-hydroxy acid derivative corresponds to the radical (enediol/hydroxyacrylic structure with OH, OH, =O)

and the stereoisomers, organic or mineral salts, and solvates thereof, and
   (ii) raising the temperature of the keratin fibres, using a heating means, to a temperature of between 110 and 250° C.;
   wherein the hair-relaxing composition comprises ureas of formula (I) at a concentration greater than or equal to 2 M;
   wherein the hair-relaxing composition comprises α-hydroxy acid derivatives of formula (IV) at a concentration greater than or equal to 2 M; and
   wherein the overall concentration of denaturing agents is less than or equal to 8 M.

2. A process according to claim 1, wherein the pH of the composition is less than 7.

3. A process according to claim 1, wherein the temperature is raised to a temperature of between 140° C. and 220° C.

4. A process according to claim 1, wherein the molar mass of the denaturing agents is between 40 and 600 g/mol.

5. A process according to claim 1, wherein the hair-relaxing composition further comprises at least one additional denaturing agent chosen from guanidines, α-keto acid derivatives, mono-, di-, tri-, or polyhydroxylated aromatic derivatives, cyclic or linear amides, surfactants or detergents, amidines, thioureas, urethanes, alcohols, polyols, amine oxides, metal salts, sulfamides, carboxylic acids, amino acids, and nitrogenous heterocycles of the imidazole or triazole family.

6. A process according to claim 1, wherein at least one of the denaturing agents is urea.

7. A process according to claim 1, wherein in formula (IV) R1 is hydrogen.

8. A process according to claim 1, wherein the α-hydroxy acid derivatives of formula (IV) are chosen from glycolic acid, lactic acid, malic acid, citric acid, and tartaric acid.

* * * * *